United States Patent [19]

McCarthy

[11] 4,369,790

[45] Jan. 25, 1983

[54] CATHETER

[76] Inventor: John M. McCarthy, 192 Main St., Port Washington, N.Y. 11050

[21] Appl. No.: 241,001

[22] Filed: Mar. 5, 1981

[51] Int. Cl.³ .......................................... A61M 25/00
[52] U.S. Cl. .................................................. 604/280
[58] Field of Search .............. 128/349, 348, 350, 243, 128/DIG. 16

[56] References Cited

U.S. PATENT DOCUMENTS

| | | | |
|---|---|---|---|
| 1,207,479 | 12/1916 | Bisgaard | 128/349 |
| 2,230,226 | 2/1941 | Auzin | 128/349 |
| 2,574,840 | 11/1951 | Pieri et al. | 128/349 |
| 2,649,092 | 8/1953 | Wallace | 128/349 |
| 3,397,699 | 8/1968 | Kohl | 128/349 |
| 3,692,029 | 9/1972 | Adair | 128/349 R |
| 3,799,172 | 3/1974 | Szpur | 128/349 R |
| 3,924,633 | 12/1975 | Cook et al. | 128/349 R |

FOREIGN PATENT DOCUMENTS 2312264 12/1976 France ................................ 128/349

*Primary Examiner*—Stephen C. Pellegrino
*Attorney, Agent, or Firm*—Lee C. Robinson, Jr.

[57] ABSTRACT

A catheter includes an elongated tubular member having a closed distal end, an open proximal end and a maximum outer diameter of 2 mm; exactly two longitudinally extending slits of unequal lengths in the tubular member adjacent the distal end thereof, which form two distortable strands; a flexible wire secured to the distal end and extending inside the tubular member towards the proximal end thereof for retracting the distal end with respect to the proximal end; and an obturator secured to the free end of the wire for actuating the wire to retract the distal end with respect to the proximal end so as to outwardly bias the two distortable portions to anchor the distal end in the bladder of a patient, and for providing a fluid impervious seal to the open proximal end when the distal end is in its unretracted position with respect to the proximal end.

11 Claims, 6 Drawing Figures

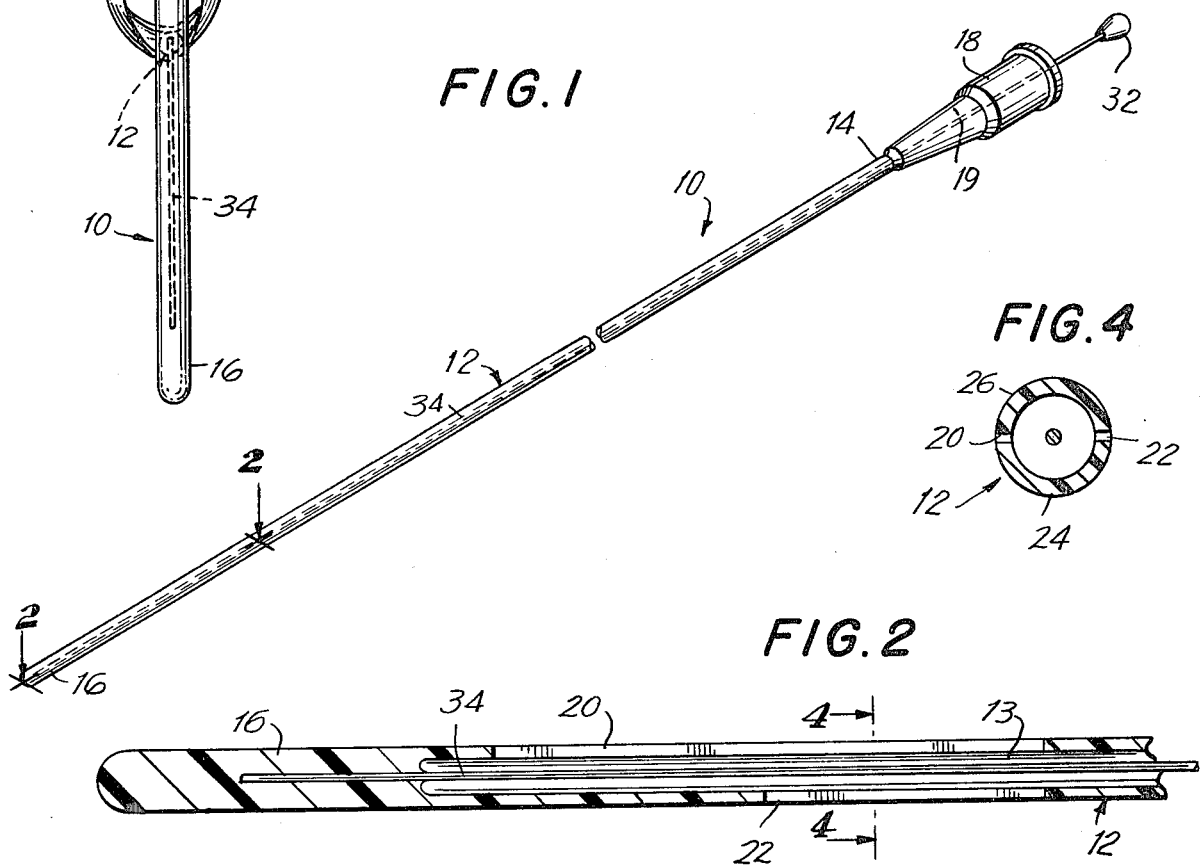
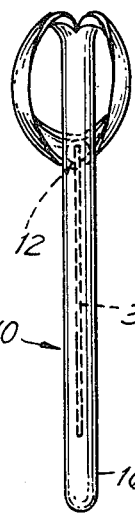
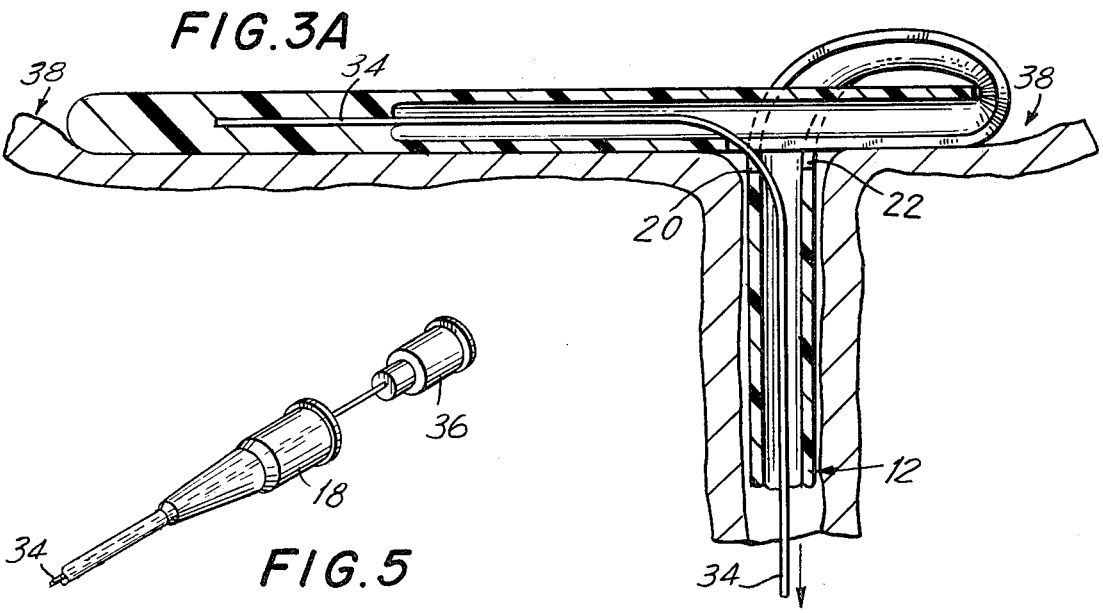

CATHETER

BACKGROUND OF THE INVENTION

1. Field of the Invention

The present invention relates generally to catheters and, more particularly, is directed to a catheter of the type having its distal end adapted to be anchored in a body cavity.

2. Description of the Prior Art

With catheters of the type adapted to be inserted into the urinary bladder and retained therein, it is generally desirable to construct the catheter tube with as small an outer diameter as possible so as to reduce discomfort to the patient during insertion, use and withdrawal. One type of catheter which has conventionally been used includes a main fluid passage through which the urine flows and a smaller parallel fluid passage which extends to an inflatable retention balloon molded as an integral part of the inlet end portion of the catheter. However, such "balloon" type catheters generally require a relatively large diameter with the attendant discomfort to the patient.

It has therefore been proposed, as shown, for example, in U.S. Pat. No. 2,649,092, to provide a single fluid passage or tubular portion having a series of longitudinally extending slits extending along the tubular portion adjacent its distal end. A wire is attached to the distal end of the tubular portion and, when pulled towards the proximal end, causes the strands of the tubular portion to extend outwardly so as to anchor the distal end in the bladder. At such time, urine flows through the slits into the tubular portion and out of the catheter.

Such prior catheters have generally been formed with at least three slits of equal length for anchoring the distal end thereof in the bladder. However, the use of three or more slits may not provide the catheter with a satisfactory anchoring characteristic. This is because the width of each strand is decreased as the number of strands increases. Further, although this type of catheter generally has a smaller outer diameter than that of the "balloon" type catheters, the outer diameter cannot be made too small without further reducing the width of the strands. For example, in the slitted catheters employed heretofore it was difficult to reduce the outer diameter of the catheter below about 4 mm, which still resulted in substantial discomfort to the patient and for small children rendered the catheter extremely difficult if not impossible to use.

It is also desirable to provide good drainage from the bladder to the catheter tube. In this regard, the above known catheters having three or more slits probably provide satisfactory drainage, wherein the urine is passed through the slits into the catheter tube. However, if only one slit is provided, unsatisfactory drainage may result, particularly in the case where solid or partially solid elements in the urine block the one slit.

OBJECTS AND SUMMARY OF THE INVENTION

Accordingly, it is an object of this invention to provide a catheter that provides good drainage while also providing a good anchoring capability of the distal end of the catheter in the bladder.

It is another object of this invention to provide a catheter having exactly two slits adjacent the distal end thereof so as to provide good drainage and a good anchoring characteristic.

It is still another object of this invention to provide a catheter having exactly two slits adjacent the distal end thereof in which one slit is shorter than the other so as to provide an optimum anchoring characteristic.

It is yet another object of this invention to provide a catheter having a substantially reduced outer diameter from known catheters.

In accordance with an aspect of this invention, a catheter includes an elongated tubular member having a closed distal end and an open proximal end, exactly two longitudinally extending slits in the tubular member adjacent the distal end thereof, flexible means secured to the distal end and extending inside the tubular member towards the proximal end thereof for retracting the distal end with respect to the proximal end, and actuator means secured to the free end of the flexible means for actuating the flexible means to retract the distal end with respect to the proximal end.

In a preferred embodiment of this invention, the two longitudinally extending slits are diametrically opposed to each other along the circumference of the tubular member and are of different lengths. In addition, the actuator means includes an obturator which also provides a fluid impervious seal at the open proximal end of the tubular member when the catheter is in its unretracted configuration.

The above, and other, objects, features and advantages of the invention with become apparent from the following detailed description of illustrative embodiments of the invention which is to be read in connection with the accompanying drawings.

BRIEF DESCRIPTION OF THE DRAWINGS

FIG. 1 is a perspective view of a catheter according to one embodiment of this invention;

FIG. 2 is a cross-sectional view of the distal end of the catheter of FIG. 1, taken along line 2—2 thereof;

FIG. 3A is a cross-sectional view of the distal end of the catheter of FIG. 2 in its retracted position when anchored in a bladder;

FIG. 3B is a distal end view of the catheter in the position of FIG. 3A;

FIG. 4 is an end cross-sectional view of the distal end of the catheter of FIG. 2, taken along line 4—4 thereof; and FIG. 5 is a perspective view of another embodiment of the proximal end of a catheter according to the present invention.

DETAILED DESCRIPTION OF THE PREFERRED EMBODIMENTS

Referring to the drawings in detail, and initially to FIG. 1 thereof, there is generally shown a catheter 10 according to one embodiment of this invention. As shown therein, catheter 10 includes an elongated tubular member 12, having a length, for example, of 22 cm, and preferably made from a flexible plastic material, such as polyurethane or polyethylene, preferably Teflon or silicone coated. Unlike known catheters, the outer diameter of the catheter according to the present invention has a maximum outer diameter of 2 mm (6 French) and can be constructed with an outer diameter as small as 1.33 mm (4 French). This latter diameter is the minimum diameter necessary for adequate drainage. In other words, the catheter according to the present invention is considerably smaller than conventional catheters so as to provide substantially less discomfort to the patient and has particular applicability for use with newborn and infant children with unique urinary problems.

Catheter 10 is constructed with a central bore 13 for drainage. Catheter 10 further includes a proximal end 14 which is open and a distal end 16 which is closed, the latter end being adapted to be inserted into a body cavity, for example, into the bladder through the urethra. Distal end 16 is further shown in FIG. 2 to include a rounded end for easy penetration into the body cavity without substantial discomfort to the patient. Further, a tubular hub 18, which is preferably tapered, for example, at a 60° angle, and has a central bore 19, is connected to proximal end 14 of tubular member 12 so as to be in fluid communication therewith. The hub 18 has an inside diameter greater than the inside diameter of the tubular member 12 and is open at both ends to provide adequate drainage of the urine.

A pair of slits 20 and 22 is provided in the tubular member 12 adjacent its distal end. The slits 20 and 22 are in at least partially overlapping relationship with each other in the longitudinal direction and are diametrically arranged on the tubular member 12 so as to form two distortable or flexible strands 24 and 26 which, as will hereinafter be discussed, are used for anchoring the distal end 16 of the tubular member in the bladder. By arranging the slits 20 and 22 diametrically, the strands 24 and 26 are of equal width around the periphery of the tube.

The proximal ends of the slits 20 and 22 (the right ends as viewed in FIG. 2) are located in equidistant relationship with the distal end 16 of the catheter. The distal end of the slit 20 is located as close as practical to the end 16, while the distal end of the slit 22 is spaced a short distance therefrom. The arrangement is such that the slit 22 is substantially shorter than the slit 20 and has a length that advantageously is about one-half to about three-fourths the length of the slit 20. For best results the length of the slit 20 should be between about three centimeters and about five centimeters with a correspondingly shorter length for the slit 22.

A flexible wire 34 formed, for example, from stainless steel, nylon or polyethylene, is secured to the distal end 16 of the tubular member 12. The wire 34 extends through the central bores 13 and 19 of the tubular member 12 and the hub 18, respectively, and protrudes out of the catheter. The wire 34 is preferably coated with plastic for safety reasons.

An actuator member 32, in the form of an enlarged bulbous portion, is secured to the free end of wire 34. Thus, when the actuator member 32 is pulled by the user, the distal end 16 is caused to retract towards the proximal end 14 of the tubular member 12. This, in turn, results in the distortable strands 24 and 26 being flexed or biased outwardly.

In use, the distal end 16 of the catheter 10 is inserted into the bladder of a patient through the urethra. After the end 16 has been inserted into the bladder, the hub 18 is firmly held in one hand, and a light tension is applied to the wire 34 by pulling firmly on the actuator member 32 with the other hand. Since the slits 20 and 22 are formed near the distal end 16 of the catheter 10, the catheter is caused to distort so as to form a T-configuration, as shown in FIG. 3, which results in the anchoring of the distal end 16 in the bladder 38 of the patient. It will be observed from FIG. 3 that one of the arms of the T-shaped distal end of the catheter is shorter than the other arm. Such a configuration results from the use of slits of unequal length and further enhances the anchoring of the catheter within the bladder. The catheter may be fixed in this configuration by a standard connecting device after as little as 3 mm of wire has been exposed at the proximal end.

With the catheter in position, the urine in the bladder may flow through the slits 20 and 22 into the central bore 13 of the tubular member 12 and out proximal end 14 of the catheter to be drained therefrom through the hub 18. When it is desired to remove the catheter from the body, the actuator member 32 is merely released or is pushed toward the hub 18, thus returning the distal end of the catheter 10 to the straightened configuration shown in FIGS. 1 and 2. The catheter may then be simply and easily removed from the body.

By providing two unequal-length slits in the catheter, adequate drainage is obtained and yet the width of the strands between the slits is sufficiently large to result in good anchoring of the distal end in the bladder. The outer diameter of the catheter may be made much smaller than that of conventional catheters so as to reduce discomfort to the patient and to be particularly applicable with newborn and infant children and for use in vetinary medicine. In addition, the use of two slits of different lengths provides a substantially greater anchoring characteristic than even two slits having equal lengths.

Further, when catheter 10 is in its unretracted configuration, as shown in FIGS. 1 and 2, and is inserted into the bladder, it is desirable that no urine leak out of the catheter from slits 20 and 22. Thus, in accordance with another embodiment of the present invention, as shown in FIG. 5, actuator member 32 is replaced by an obturator 36 secured to the free end of wire 34. In this manner, when catheter 10 is in its configuration shown in FIGS. 1 and 2, obturator 36 is inserted, in a snug-fitting relation, into the enlarged open end of hub 18 to prevent any fluid from escaping therefrom.

Having described specific preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A catheter comprising:
   an elongated tubular member having a closed distal end and an open proximal end;
   exactly two longitudinally extending slits in said tubular member adjacent the distal end thereof, one of said slits having a length greater than that of the other of said slits;
   flexible means secured to the distal end and extending inside the tubular member towards the proximal end thereof for retracting said distal end with respect to said proximal end; and
   actuator means secured to the free end of said flexible means for actuating said flexible means to retract said distal end with respect to said proximal end.

2. The catheter according to claim 5; in which said flexible means includes a wire formed from one of stainless steel, polyethylene, and nylon.

3. The catheter according to claim 5; in which said tubular member has a maximum outer diameter of 2 mm.

4. The catheter according to claim 5; in which said two slits are diametrically opposed along the circumference of said tubular member.

5. A catheter comprising:

an elongated tubular member having a closed distal end and an open proximal end;

exactly two longitudinally extending slits in said tubular member adjacent the distal end thereof, one of said slits having a length greater than that of the other of said slits;

flexible wire means secured to the distal end and extending inside the tubular member towards the proximal end thereof for retracting said distal end with respect to said proximal end; and obturator means secured to the free end of said flexible means for actuating said flexible means to retract said distal end with respect to said proximal end and for providing a fluid impervious seal to said open proximal end when said distal end is in its unretracted position with respect to said proximal end.

6. A catheter comprising:

an elongated tubular member having a closed distal end and an open proximal end;

exactly two longitudinally extending slits in said tubular member adjacent the distal end thereof, said slits being circumferentially spaced from each other along said tubular member and said slits being formed in at least a partially overlapping relation to each other in the longitudinal direction of said tubular member, with one of said slits having a length greater than that of the other of said slits;

flexible means secured to the distal end and extending inside the tubular member towards the proximal end for retracting said distal end with respect to said proximal end; and actuator means secured to the free end of said flexible means for actuating said flexible means to retract said distal end with respect to said proximal end.

7. A catheter comprising:

an elongated tubular member having a closed distal end and an open proximal end;

a pair of longitudinally extending slits of different lengths in said tubular member adjacent the distal end thereof, the slits separating the tubular member adjacent its distal end to form two distortable portions;

flexible means having a first end secured to the distal end of the tubular member and a second, free end, the flexible means extending inside the tubular member towards the proximal end thereof for retracting said distal end with respect to said proximal end; and actuator means secured to the free end of said flexible means for actuating said flexible means to retract said distal end with respect to said proximal end and thereby outwardly bias said two distortable portions.

8. A catheter comprising:

an elongated tubular member having a closed distal end and an open proximal end;

a pair of longitudinally extending slits of different lengths in said tubular member adjacent the distal end thereof, the slits separating the tubular member adjacent its distal end to form two distortable portions, the lenght of one of said slits being not less than about one-half and not more than about three-fourths the length of the other slit;

flexible means having a first end secured to the distal end of the tubular member and a second, free end, the flexible means extending inside the tubular member towards the proximal end thereof for retracting said distal end with respect to said proximal end; and actuator means secured to the free end of said flexible means for actuating said flexible means to retract said distal end with respect to said proximal end and thereby outwardly bias said two distortable portions.

9. A catheter comprising:

an elongated tubular member having a closed distal end and an open proximal end;

a pair of logitudinally extending slits of different lengths in said tubular member adjacent the distal end thereof, the slits separating the tubular member adjacent its distal end to form two distortable portions, the ends of said slits adjacent the distal end of said tubular member being spaced different distances from said distal end;

flexible means having a first end secured to the distal end of the tubular member and a second, free end, the flexible means extending inside the tubular member towards the proximal end thereof for retracting said distal end with respect to said proximal end; and actuator means secured to the free end of said flexible means for actuating said flexible means to retract said distal end with respect to said proximal end and thereby outwardly bias said two distortable portions.

10. A catheter according to claim 9; wherein said two distortable portions and the remainder of said tubular member substantially form a T-configuration when said two distortable portions are outwardly biased.

11. A catheter according to claim 10; wherein one of the arms of the T-confirguration is shorter than the other arm.

* * * * *